(12) United States Patent
Yamaoka et al.

(10) Patent No.: US 7,396,642 B2
(45) Date of Patent: Jul. 8, 2008

(54) METHODS OF SCREENING FOR A COMPOUND THAT ENHANCES THERMOGENESIS

(75) Inventors: Kazuyoshi Yamaoka, Tokyo (JP); Kenichiro Takagi, Tokyo (JP); Kenichiro Kataoka, Tokyo (JP); Masanori Yamamoto, Tokyo (JP); Toshihiro Chikanishi, Tokyo (JP)

(73) Assignee: Teijin Limited, Osaka (JP)

(*) Notice: Subject to any disclaimer, the term of this patent is extended or adjusted under 35 U.S.C. 154(b) by 447 days.

(21) Appl. No.: 10/483,627

(22) PCT Filed: Jul. 17, 2002

(86) PCT No.: PCT/JP02/07277

§ 371 (c)(1),
(2), (4) Date: Jan. 14, 2004

(87) PCT Pub. No.: WO03/008967

PCT Pub. Date: Jan. 30, 2003

(65) Prior Publication Data

US 2004/0265817 A1    Dec. 30, 2004

(30) Foreign Application Priority Data

Jul. 17, 2001  (JP)  ............... 2001-216502

(51) Int. Cl.
C12Q 1/00  (2006.01)
C12Q 1/68  (2006.01)
G01N 33/53  (2006.01)

(52) U.S. Cl. .................. 435/4; 435/6; 435/7.1
(58) Field of Classification Search ............ None
See application file for complete search history.

(56) References Cited

U.S. PATENT DOCUMENTS 6,300,362 B1   10/2001   Liu et al.
6,300,364 B1   10/2001   Shimokawa et al.

FOREIGN PATENT DOCUMENTS

| WO | WO 96/33724 A1 | 10/1996 |
| WO | WO 97/27847 A1 | 8/1997 |
| WO | WO 97/28149 A1 | 8/1997 |
| WO | WO 99/04815 A1 | 2/1999 |
| WO | 99-04815 A1 | 4/1999 |
| WO | WO 01/00603 A1 | 1/2001 |

OTHER PUBLICATIONS

Itsuro Nagase et al., 'Up-regulation of uncoupling protein 3 by thyroid hormone, peroxisome proliferators-activated receptor ligands and 9-cis retinoic acid in L6 myotubes' FEBS Letters, 1999, vol. 461, No. 3, pp. 319 to 322.

Kazutomo Imabori, Seikagaku Jiten (Dai 2 han), Tokyo Kagaku Dojin, Apr. 1, 1995, pp. 792 to 793.

Albert L. Lehninger, Jiro Koyama et al., Lehninger no Shin Seikagaku (Jo), Kabushiki Kaisha Hirokawa Shoten, Oct. 25, 1986, pp. 533 to 534.

Hebe M. Guardiola-Diaz et al., 'Rat Peroxisome Proliferator-activated Receptors and Brown Adipose Tissue Function during Cold Acclimatization' The Journal of Biological Chemistry, 1999, vol. 274, No. 33, pp. 23368 to 23377.

Steven D Clarke et al., 'Peroxisome proliferatoractivated receptors: a family of lipid-activated transcription factors' American Journal of Clinical Nutrition, 1999, vol. 70, No. 4, pp. 566 to 571.

Chevillotte, Emmanuel, et al. "The Regulation of Uncoupling Protein-2 Gene Expression by ω -6 Polyunsaturated Fatty Acids in Human Skeletal Muscle Cells Involves Multiple Pathways, Including the Nuclear Receptor Peroxisome Proliferator-activated Receptor β" The Journal of Biological Chemistry; vol. 276, No. 14, Issue of Apr. 6, 2001, pp. 10853-10860; by The American Society for Biochemistry and Molecular Biology, Inc.

Jerome Aubert, et al., "Up-Regulation of UCP-2 Gene Expression by PPAR Agonists in Preadipose and Adipose Cells," *Biochemical and Biophysical Research Communications*, vol. 238, No. 2, pp. 606-611, Aug. 14, 1997, XP-002953881.

Joel Berger, et al. "Novel Peroxisome Proliferator-activated Receptor (PPAR) γ and PPARδ Ligands Produce Distinct Biological Effects," *The Journal of Biological Chemistry*, vol. 274, No. 10, Mar. 5, 1999, pp. 6718-6825, XP-002158742.

Timothy M. Willson, et al. "The PPARs: From Orphan Receptors to Drug Discovery," *Journal of Medicinal Chemistry*, vol. 43, No. 4, Feb. 24, 2000, pp. 527-550, XP-001066309.

Rajnish A. Gupta, et al. "Prostacyclin-mediated activation of peroxisome proliferator-activated receptor δ in colorectal cancer," *Proceedings of the National Academy of Sciences of the Unites States of America*, vol. 97, No. 24, pp. 13275-13280, XP002972848.

*Primary Examiner*—Ruixiang Li
(74) *Attorney, Agent, or Firm*—Sughrue Mion, PLLC

(57) ABSTRACT

The present invention provides a method for screening a substance having a thermogenesis enhancing effect containing a compound having an effect activating PPAR δ, an agent containing the compound, and an agent having antidiabetic, antiobestic or visceral accumulated fat-lowering function.

The present invention provides an agent containing a compound having an effect activating PPAR δ, which is a peroxisome proliferator activated receptor, and having effects which enhances nonshivering thermogenesis (nST), specifically enhances uncoupling respiration in mitochondria of cells in an adipose tissue or the like, or proton leak in inner membranes of mitochondria, and increases the amount of expression of UCP1, and provides an antidiabetic agent, an antiobestic gent and a visceral accumulated fat-lowering agent containing the compound. Further, the present invention provides a method for screening the compound by measuring a PPAR δ activating effect.

9 Claims, 3 Drawing Sheets

METHODS OF SCREENING FOR A COMPOUND THAT ENHANCES THERMOGENESIS

TECHNICAL FIELD

The present invention relates to a method for screening a substance having a thermogenesis enhancing effect by measuring an effect for activating peroxisome proliferator activated receptor δ (PPARδ) and an agent containing a compound having thermogenesis enhancing effect, which has a PPAR δ activating effect. Further, the present invention relates to an agent which specifically enhances uncoupling protein (UCP)-caused uncoupling respiration or proton leak in mitochondrial inner membrane (hereafter, this is generically called proton leak) among functions of mitochondria, which are organelles in energy metabolism (respiration) cells using fatty acids and pyruvate as substrates. Further, the present invention relates to an antidiabetic agent, an antiobestic agent, and a visceral accumulated fat-lowering agent or visceral fat accumulation-inhibiting agent.

BACKGROUND ART

The energy metabolism-regulating system in vivo consists of a food ingestion-regulating system and an energy consumption-regulating system. The energy consumption-regulating system participates in two categories of energy consumptions, that is, energy consumption for basal metabolism in order to sustain life and the other energy consumption. The main energy consumption under the latter category is non-shivering thermogenesis (nST), which is thermogenesis, and whose functional significance is maintenance of body temperature immediately after birth, during exposure to cold, at the end of hibernation, etc., and prevention of obesity and glycolipid metabolism disorder by consuming excess energy attributable to overeating, etc. Especially, in mammals and birds, which are homothermals, particularly in small animals, nST is important for maintaining body temperature. In the mechanism to induce nST, proton leak in mitochondria, that is, the participation of the electron transport system of the respiration chain in cells and ATP synthesis is important.

In a brown adipose tissue (BAT), a specific protein called an uncoupling protein 1 (UCP1) having a molecular weight of 32 kD and consisting of about 300 amino acids exists in the membranes of mitochondria. The protein has a function to uncouple the ATP synthesis from the electron transport system of the respiration chain of brown adipocytes (BA). UCP1 consists of a trebly repeating structure of a domain composed of approximately 100 amino acids and has 2 transmembrane regions in each domain, 6 sites in total. These transmembrane regions form channels in membranes of mitochondria.

UCP1 is a carrier that transports protons. Proton channels formed by UCP1 and others exhibit a function which allows protons to permeate freely in accordance with an electrochemical gradient to release heat. This is nST. That is, nST causes the uncoupling by proton permeation through proton channels, and the uncoupling reduces ATP synthesis, so that respiration in mitochondria is activated in order to keep the ratio of ATP to ADP constant. As a result, a large amount of fats and sugar are oxidized to generate heat.

The physiological significance of UCP1 is that it plays an important role in body temperature keeping immediately after birth, during exposure to cold, etc., and studies using transgenic mice have also elucidated that it participates in the prevention of obesity. The correlation of UCP1 with the development, progression and persistence of obesity has been suggested by the fact that there is a reduction in UCP1 expression in various obesity models. For example, it is confirmed that obesity develops without overeating in BAT-reduced transgenic mice (Lowell, et al., Nature, 366, 740-742 (1993)). Further, the reduction in body fat and the resistance against diet-induced obesity due to high fat-loaded meal were observed in mice which were forced to express a large amount of UCP1 by inserting UCP1 gene into a promoter of adipocyte-specific gene, aP2 (Kopecky et al., J Clin Invest, 96, 2914-2923 (1995)). Furthermore, the decrease in body temperature keeping function during the exposure to cold, obesity due to the increase of body fat, and insulin resistance were observed in mice whose UCP1 expression had been suppressed to ⅓(Lowell B. B., et al., Nature, 366, 740-742 (1993)). Further, UCP1 knockout mice were non-tolerant to cold (Enerback S. et al., Nature, 387, 90-94 (1997)). As shown above, it has become clear from animal experiments that UCP1 has important role in body temperature regulation and energy consumption as a thermogenetic molecule, and is closely related to obesity.

The amount of UCP1 expression is regulated mainly by the endonuclear gene transcription level, and UCP1 gene expression is increased by the elevation in cAMP concentrations (Saito et al., Saishin Igaku, 52, 1095-1096 (1997)).

Approximately 20 to 40% of intracellular energy consumption is considered to be produced by proton leak in mitochondrial inner membranes. Moreover, the majority of nST has been considered to be produced in skeletal muscles and white adipose tissues (WAT) in adult humans and other animals having little BAT. Based on the above-mentioned facts, it has been estimated that UCP exists in tissues other than BAT. cDNA cloning of UCP2 from other tissues than BAT was reported in succession by two groups in 1997 (Fleury, et al., Nature Genet, 15, 269-272 (1997): and Gimeno et al., Diabetes 46, 900-906 (1997)).

Human UCP2 shows 59% homology with human UCP1, and forms channels having 6 transmembrane regions as in UCP1, and it has purine nucleotide-binding sites. UCP2 differs from UCP1 in that it is widely expressed in the systemic tissue and is expressed in particularly high concentrations in the lung and pancreas, and expression is also detected in the heart, the liver, the brain, kidneys, testicles, WAT, BAT and skeletal muscles.

Regarding UCP2 function, the upregulation of UCP2 gene expression in adipose tissues around epididymids is observed in high fat diet-loaded mice. However, it was reported that UCP2 knockout mice were normal in body temperature keeping function under cold conditions (Arsenijevic D. et al., Nature Genet, 26, 387-388 (2000)). Further, an extensive upregulation of expression of UCP2 in the brown adipate tissue, which was considered compensation, was observed in the above-mentioned UCP1 knockout mice, and the mice were non-tolerant to cold (Enerback S. et al., Nature, 387, 90-94 (1997)). Further, it was shown that UCP2 suppressed insulin secretion via changing of intracellular ATP concentration in pancreas β cells (Zhang C.-Y. et al., Cell, 105, 745-755 (2001)). This is a disadvantageous property for diabetic therapy. As mentioned above, for UCP2, up to the present time, the relation to energy consumption/obesity has not been made clear although uncoupling function as proton channel has been confirmed.

The excessive energy in vivo is accumulated at first preferentially as visceral fat (especially, as mesenteric fat). Compared with fats at other sites (especially, subcutaneous fat), the visceral fat is apt to receive adipokinetic effect, and it is quickly decomposed and consumed. The visceral fat (obesity) is regarded as a multiple risk factor to cause life style-related diseases (adult diseases). The reason for this is that fatty acids secreted from white adipocytes (WA) in WAT are flown directly into the liver via the portal vein to accelerate insulin resistance and fat synthesis, and as a result, to induce sugar resistance abnormalities, high blood pressure and hyperlipemia, and these are finally complicated to cause arteriosclerosis. Accordingly, the inhibition of accumulation of the visceral fat and the reduction of accumulated visceral fat are expected to be effective for preventing the occurrence of life style-related diseases such as diabetics in adult humans and treating them.

A peroxisome proliferator activated receptor (PPAR) is considered as a member of a nuclear receptor (nuclear hormone receptor) super family from its structure and others. Up to now, three kinds of PPAR subtypes called PPAT α, PPAR δ (also called NUC-1, PPAR β or FAAR) and PPAR γ have been identified, and their genes (cDNA) have been cloned (Lemberger et al., Annu. Rev. Cell. Dev. Biol., 12, 335-363 (1996)).

It was reported that, fibrate agents having a ligand effect on PPARα, among the three kinds of PPARs, clinically show a strong lowering effect on serum triacylglycerol level (Forman et al., Proc. Natl. Acad. Sci. USA, 94, 4312-4317 (1997)).

PPAR γ is expressed especially in adipose tissues, and it was disclosed that the PPAR γ is a factor deeply implicated in regulating differentiation of adipocytes (Tontonoz et al., Genes and Development, 8, 1224-1234 (1994); and Tontonoz et al., Cell, 79, 1147-1156 (1994)). Various kinds of thiazolidinedione derivatives show a hypoglycemic effect in animal model of non-insulin-dependent diabetes mellitus (NIDDM) and are expected as new therapeutic agents for NIDDM having an insulin resistance breaking effect. A recent study demonstrated that the thiazolidinedione derivatives have also an effect as a ligand of PPAR y and activate specifically the PPAR γ (Lehman et al., J. Biol. Chem., 270, 12953-12956 (1995)).

However, physiological function of PPAR δ is not made clear yet (Willson et al., J. Med. Chem., 43 (4), 527-550 (2000)). WO97/28149 description disclosed that a PPAR δ ligand has a blood HDL increasing effect, and WO9904815 description disclosed that the administration of a PPAR δ-activating substance lowers a cholesterol level. But, there is no disclosure nor suggestion for the correlation between PPAR δ and a thermogenesis enhancing effect, and that between PPAR δ and an uncoupling protein.

Furthermore, it is known that an unsaturated fatty acid such as arachidonic acid, carbaprostacyclin (cPGI), and L-165041 (4-(3-(2-propyl-3-hydroxy-4-acetyl-phenoxy)propyloxy)-phenoxyacetic acid) increase the expression of UCP2 (The Journal of Biological Chemistry, Vol. 276, No. 14, Issue of April 6, pp. 10853-10860, 2001). However, there is no report on the correlation between UCP1 and PPAR δ.

DISCLOSURE OF THE INVENTION

The purpose of the present invention is to provide a method for screening a substance having a thermogenesis enhancing effect and an agent containing the substance as an active ingredient. Further, the purpose of the present invention is to provide an antidiabetic agent, an antiobestic agent, and an agent for lowering the amount of visceral fat accumulation or for inhibiting visceral fat accumulation.

The inventors of the present invention paid attention on a thermogenesis enhancing effect due to the stimulation of nST in the energy consumption-regulating system in vivo. They intended to enhance uncoupling respiration in mitochondria; to enhance proton leak in mitochondria of BAT, which is relatively small as an nST tissue, and further of WAT, and to enhance the function of UCP1, a homologue of uncoupling proteins, and thereby to improve their efficiencies.

The inventors of the present invention pursued zealous studies to solve such problems as mentioned above, and found that carbaprostacyclin (cPGI 6,9α-methylene-11α, 15S-dihydroxy-prosta-5E, 13E-dien-1-oic acid) and Iloprost (5-{(E)-(1S, 5S, 6R, 7R)-7-hydroxy-6-[(E)-(3S, 4RS)-3-hydroxy-4 -methyl-5-octen-6-inyl]-bicyclo [3.3.0]-octan-3-ylidene} pentenoic acid), which are nonspecific PPAR ligands, had a UCP1 expression-enhancing effect in skeletal muscle cells or adipocytes.

This new finding was combined with the findings that fibrate compounds and Wy14643, which are ligands for PPAR α, and thiazolidinedione compounds, which are a ligand for PPAR γ, hardly exhibit a UCP1 expression enhancing effect. Based on this combined finding, the inventors assumed that PPAR δ mainly participates in the UCP1 expression enhancing effect, and they pursued further studies on compounds having a PPAR δ-activating effect.

Resultingly, they disclosed that substances having a PPAR δ-activating effect showed the UCP1 expression enhancing effect, from experiments using skeletal muscle cells or adipocytes of a human or a rodent.

Further, based on the fact that the expression of UCP gene is regulated by PPAR δ, the inventors of the present invention found that a substance having a thermogenesis enhancing effect, which enhances the expression of UCP1 genes and promotes an nST function, can be screed by measuring the PPAR δ-activating effect.

Accordingly, the present invention includes following items.

(1) A method for screening a substance having a thermogenesis enhancing effect, by measuring a PPAR δ-activating effect.

(2) A method for screening a substance having an effect for enhancing uncoupling respiration in mitochondria, by measuring a PPAR δ-activating effect.

(3) A method for screening a substance having an effect for enhancing proton leak in inner membranes of mitochondria, by measuring a PPAR δ-activating effect.

(4) A method for screening a substance increasing the expression of UCP1 in mitochondria-containing cells, by measuring a PPAR δ-activating effect.

(5) A method for screening a substance enhancing fatty acid β-oxidation, by measuring a PPAR δ-activating effect.

(6) The method for screening the substance according to any one of items (1) to (5), using a reporter gene.

(7) The method for screening a substance having a thermogenesis enhancing effect according to item (6), wherein the method includes processes of the following ① to ③;

① a process in which a substance having a PPAR δ-activating effect is brought into contact with and/or introduced into cells expressing a UCP1 gene, ② a process in which the amount of expression of said UCP1 gene in said cell is measured, and ③ a process in which a compound increasing the amount of expression of said UCP1 gene in said cell is screened.

(8) The method according to item (7), wherein the cell expressing said UCP1 gene is an adipocyte or a skeletal muscle cell.

(9) The method according to item (7), wherein the cell expressing said UCP1 gene is an adipocyte.

(10) An agent having a thermogenesis enhancing effect, wherein the agent contains a substance having a PPAR δ-activating effect as an active ingredient.

(11) An agent enhancing uncoupling respiration in mitochondria, wherein the agent contains a substance having a PPAR δ-activating effect as an active ingredient.

(12) An agent enhancing proton leak in internal membranes of mitochondria, wherein the agent contains a substance having a PPAR δ-activating effect as an active ingredient.

(13) An agent increasing the amount of expression of UCP1 in mitochondria-containing cells, wherein the agent contains a substance having a PPAR δ-activating effect as an active ingredient.

(14) An agent enhancing fatty acid β-oxidation, wherein the agent contains a substance having a PPAR δ-activating effect as an active ingredient.

(15) The agent according to any one of items (10) to (14), wherein said substance having a PPAR δ-activating effect is a nonspecific PPAR ligand or a PPAR δ ligand.

(16) The agent according to any one of items (10) to (14), wherein said substance having a PPAR δ-activating effect is carbaprostacyclin, iloprost or p-(3-(4-acetyl-3-hydroxy-2-propylphenoxy)propoxy)phenylacetic acid.

(17) The agent according to any one of items (11) to (13), wherein said mitochondria exist in cells of a skeletal muscle, a white adipose tissue or a brown adipose tissue.

(18) The agent according to any one of items (11) to (13), wherein said mitochondria exist in cells of a white adipose tissue or a brown adipose tissue.

(19) An antidiabetic agent, an antiobestic agent, an agent for lowering the amount of visceral fat accumulation or an agent for inhibiting visceral fat accumulation, wherein the agent contains a substance having a PPAR δ-activating effect as an active ingredient.

(20) An antidiabetic agent, an antiobestic agent, an agent for lowering the amount of visceral fat accumulation or an agent for inhibiting visceral fat accumulation, wherein said agent contains the agent according to any one of items (10) to (18) as an active ingredient.

MODE FOR CARRYING OUT THE INVENTION

Figure 1:
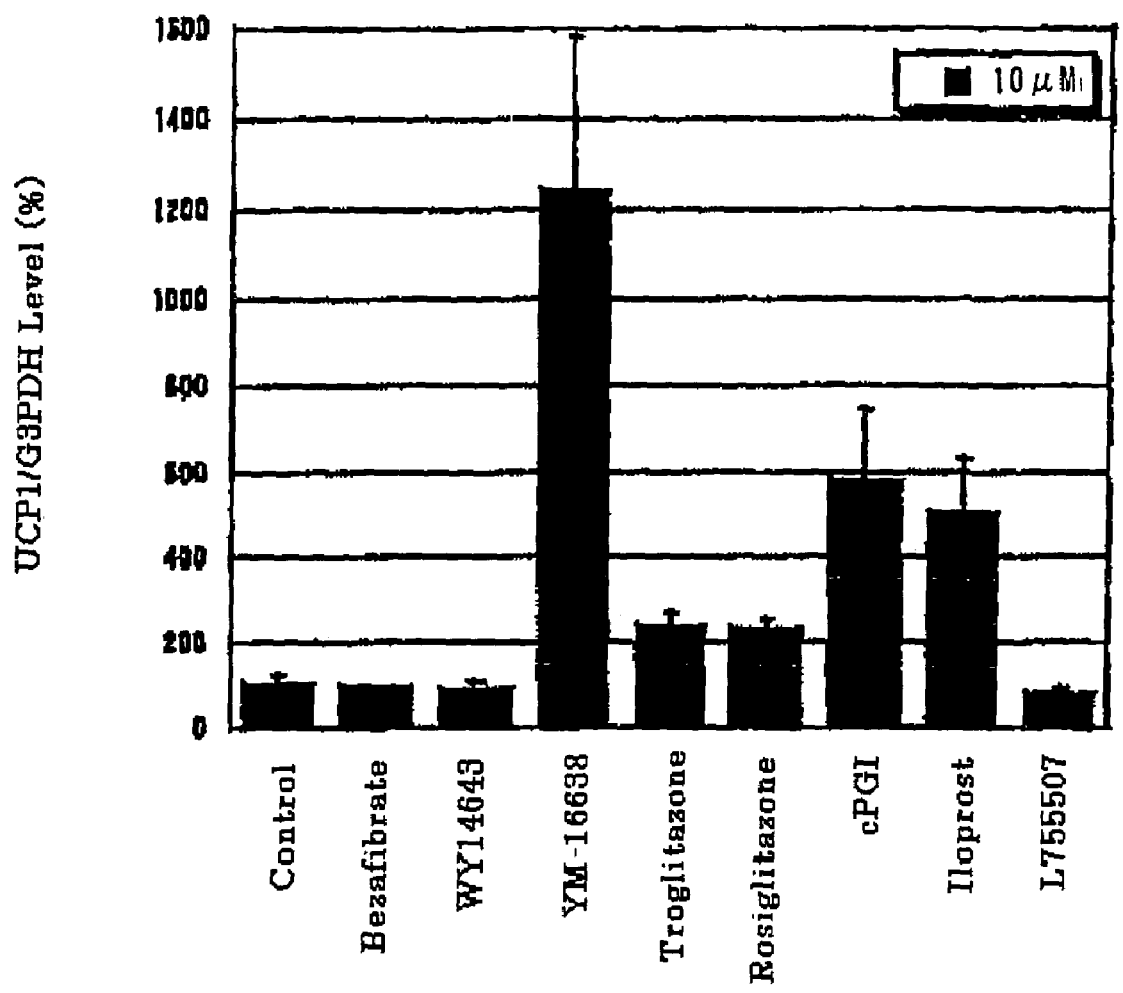
FIG. 1 shows the amount of expression of a UCP1 mRNA induced in human adipocytes by PPAR δ ligands or various kinds of test compounds.

An agent of the present invention having an effect specifically enhancing proton leak or the like in mitochondria of an nST tissue contains a compound having a PPAR δ activating effect or its derivative as an active ingredient. The agent of the present invention can be the above-mentioned active ingredient itself or an appropriate compounded matter, composition or mixture containing the ingredient. Further, a compound having a PPAR activating effect means a compound which regulates transcription-activating function of a target gene of a PPAR by binding to the PPAR as "PPAR ligand". The compound is not limited to a compound existing in nature but includes an artificially synthesized compound.

In order to elucidate the effectiveness of the above-mentioned active ingredient, the amount of mRNA of UCP1 was measured by adding various kinds of PPAR ligands to various kinds of skeletal muscle cells or adipocytes as shown in Examples. As a result, it was confirmed that PPAR δ ligands exhibited a significantly larger amount of the expression of mRNA in UCP1 than the measured PPAR α ligand and PPAR γ ligand. Examples of PPAR δ ligands include p-(3-(4-acetyl-3-hydroxy-2-propylphenoxy)propoxy)-phenylacetic acid (YM-16638) that was disclosed in the description of WO9904815 as a compound having hypocholesterolemic activity, and the like.

The degree of the binding to and/or the activation of PPAR of a substance can be determined at a high sensitivity by a simple method using a reporter gene. For example, a method using a fused protein-expressing, vector obtained by fusing a DNA binding domain of yeast transcription factor, GAL4, to a ligand binding domain of PPAR, and a method using an animal cell in which a reporter plasmid containing a reporter gene linked to a GAL4 responsive element (GAL4 binding sequence) has been transduced, are known (WO96/33724; Lehmann et al., J. Biol. Chem., 270, 12953-12956 (1995); and Willson et al., J. Med. Chem., 39, 665-668 (1996)). The method using a reporter gene works as follows. At first, when a test compound is, for example, a substance which binds to or activates PPAR, the test compound binds to a ligand binding domain of the PPAR of GAL4. Hereupon, a DNA binding domain of the GAL4, which is fused to the ligand binding domain of PPAR, binds to a GAL4 responsive element of a reporter plasmid, so that the expression of the reporter gene is promoted. By measuring the activity or the like of a protein expressed by the reporter gene, that is, by detecting the reporter activity, it can be determined whether the test compound is a PPAR binding compound or a PPAR activating compound, or not.

Accordingly, in the screening of an unknown ligand which binds to PPAR or in an examination for determining whether a test compound is a PPAR binding ligand or not, the detection and isolation of a natural or artificially synthesized ligand becomes possible. Further, the detection of reporter activity can be appropriately performed based on the technical skill in the art with an index selected from dyeing, fluorescence, cell viability and the like depending on the kind of the reporter gene.

Further, in the method of screening in the present invention, (a) a process in which a test sample is brought into contact with or introduced into a UCP1 gene-expressing cell, (b) a process in which the amount of expression of the UCP1 gene in the cell is measured, and (c) a process in which a compound increasing the amount of the expression of the UCP1 gene in the cell is screened, are optionally added to the above-mentioned system for detecting reporter activity.

"UCP1 gene-expressing cell" which is used for screening is not specifically restricted, but especially an adipocyte such as a white adipocyte or a brown adipocyte, or a skeletal muscle cell is preferable. The cell can be primary culture cells separated from an animal tissue or an established cell line which is prepared by canceration or immortalization of the cell. As the adipocyte, for example, various kinds of adipocytes such as a human white adipocyte described in the following Examples, a rat brown adipocyte and 3T3-L1 (mouse adipocyte) can be used preferably, and as the skeletal muscle cell, for example, various kinds of skeletal muscle cells such as SkMC (human skeletal muscle cell) and C2C12 (mouse skeletal muscle cell) can be used preferably. Further, examples of UCP family (uncoupling protein homologue) gene include UCP1 gene, UCP2 gene, UCP3 gene and UCP4 gene.

In a process of the screening method of the present invention, a test sample is brought into contact with and/or introduced into cells expressing such a UCP1 gene, and the amount of expression of the UCP1 gene is measured. For measuring the amount of expression of the gene, various kinds of methods well known by those of skill in the art, can be used. The measurement of the expression of the gene can be performed by measuring the amount of DNA, RNA or protein, for example, by northern blot method (Sambrook et al., Molecular Cloning, 201-206 (1987), Cold Spring Harbor Laboratory), RT-PCR method (Shaffer et al., Anal. Biochem., 190, 292-296 (1990)) or the like.

When a significant increase in the UCP1 gene expression is detected by the measurement, the compound of the test sample is considered to have an effect to promote nST function. The expression of UCP1 is essential for the burning of fat or sugar in mitochondria of cells in nST tissue. However, the active ingredient of the present invention has an effect to significantly increase the amount of the UCP1 expression in cells of the tissue as mentioned above. From this molecular level finding, the agent of the present invention is effective for inhibiting visceral fat accumulation and for lowering the amount of visceral fat accumulation.

Actually, in order to confirm that UCP whose expression is promoted by PPAR δ ligand, can work so that the visceral fat accumulation is inhibited and reduced, that is, the burning of intracellular fat and sugar is accelerated, various kinds of PPAR ligands are added to the primary human adipocytes, and fatty acid β-oxidation, which is known as one of indexes for fatty acid burning promotion, was measured in examples. As concretely shown in the examples, the fatty acid β-oxidation was promoted proportionally to the amount of expression of UCP. It was in PPAR δ ligand that the fatty acid β-oxidation was most promoted. The agent of the present invention has functions to increase the amount of expression of inner membrane-penetrating type proteins, UCP1, in mitochondria of cells of nonshivering thermogenesis tissue such as skeletal muscle and fat, which are related to nST, and to specifically enhance uncoupling respiration, proton leak and thermogenesis in mitochondria of the above-mentioned cells. The agent of the present invention contains a compound having a PPAR δ activating effect or its derivative as an active ingredient, and it has an effect for highly expressing UCP1, wherein said effect extremely increases the amount of expression of UCP1 in cells of nST tissue such as fat and skeletal muscle as shown above. The agent of the present invention can be identified, and separated and purified with the guidance of the UCP1 expression activity. By compounding a substance thus obtained as an active ingredient, an agent for lowering the amount of visceral fat accumulation or for inhibiting visceral fat accumulation having remarkable effect especially on antiobesity can be prepared.

The agent of the present invention is useful for preventing and treating obesity especially of mammals (for example, humans, mice, rats, guinea pigs, dogs, monkeys, cats, horses, rabbits or the like) or birds since it promotes energy metabolism and fat metabolism, and decreases plasma lipid. Further, it is also useful for preventing or treating a disease complicated with obesity (for example, an adult disease such as diabetic, hypertension, hyperlipemia, arteriosclerosis or ischemic heart disease) or the like.

As a carrier of the lowering agent or inhibiting agent, an appropriate filler, binder, extender, disintegrator, surfactant, desiccant, excipient, diluent or the like can be used according to the mode of use. The shape of formulation can be appropriately decided according to the purpose of use, and it is not specifically restricted. The examples of the formulation include solid preparations such as tablets, granules, powders, pills and capsules, liquids, suspensions, emulsions and the like. It is preferable that an antidiabetic agent, an antiobestic agent, and a visceral accumulated fat-lowering agent or visceral fat accumulation-inhibiting agent thus obtained, are orally administered. The dose is appropriately decided according to the symptom or the like of the patient to be treated. Accordingly, the dose, the number of times of administration per day and the like are not specifically restricted.

EXAMPLE

The present invention will be explained further in detail hereafter with examples, while the present invention is not restricted by the examples.

In the following examples, each operation is carried out according to the methods described in "Molecular Cloning" (Sambrook, J., Fritsch, E. F. and Maniatis, T, Cold Spring Harbor Laboratory Press) as far as it is not otherwise specified.

Example 1

Influence of an Agent on the Induction of mRNA Expression of UCP1 and UCP2 in Human White Adipocytes (1) Culturing of Human White Adipocytes and Preparation of RNA Human adipocytes, undifferentiated frozen preadipocytes derived from a subcutaneous adipose tissue (Cat. No. SP-F, Lot. No. L011399), were purchased from ZenBio Corp. in USA. These were cultured in a 24-well plate, and differentiated to adipocytes according to the manufacturer's instruction. The cultured cells were used as human white adipose tissue-derived adipocytes. Concretely, the preadipocytes were cultured at 37° C. in a preadipocyte medium in a $CO_2$ incubator by using the 24-well plate until an confluent state is reached, and subsequently, the culture medium was exchanged to a differentiation medium, and the culture was continued for further 72 hr to induce differentiation. Further, the medium was exchanged to an adipocyte medium, and the culture was carried out for 14 days to obtain fully differentiated white adipocytes. The cultured cells were further subjected to culture under the following conditions.

Various kinds of test compounds were each added to a medium in such a manner that the final concentration was 10 μM, and the cells were cultured for 6 hr (n=3). The test compounds were Bezafibrate and WY14643 of a PPAR α ligand, YM-16638 of a PPAR δ ligand, Troglitazone and Rosiglitazone of a PPAR γ ligand, cPGI and Iloprost of a non-specific PPAR ligand, and L755507 of β3 adrenergic receptor agonist. A control was prepared by adding DMSO, which was the solvent for the test compounds, in such a manner that the final concentration was 0.5%, and it was cultured in the same manner as the test compounds. For each test compound or the control, the cultured cells were recovered, they were suspended in 150 μl of cells lysis buffer (RLT solution, manufactured by QIAGEN Corp.), and subsequently cells were lysed to obtain cells extract. From the cell extract, a total RNA was prepared by using an RNA preparation kit (the trade name: RNeasy total RNA Kit, manufactured by QIAGEN Corp.) according to the instruction attached to the kit.

(2) Measurement of the Amount of UCP1 mRNA Expression

By using the above-obtained total RNA (about 0.1 μg) as a template, real time polymerase chain reaction (Real Time PCR) was performed as shown below to measure the amount of UCP1 mRNA expression.

As the PCR primers for human UCP1 gene, two kinds of oligonucleotides of 5'-AACCCACAGAGGTCGTGAAAG-3' (the forward-side primer) and 5'-CGTGTAGCGAG-GTTTGATTCC-3' (the reverse-side sense primer) were used. As the PCR probe, 5'-CAGACTTCAAGCATAGAGC-CATCTCCA-3' was used. The probe was labeled with FAM, a fluorescent dye. Further, the measurement of G3PDH mRNA which was concurrently performed as 2-Reporter Assay, was curried out according to the method recommended by PE Applied Biosystems. The primers were chemically synthesized by Amersham Pharmacia Biotech, and the probes were chemically synthesized by PE Applied Biosystems (including labeling with the fluorescent dye). A reaction solution shown by Table 1 was prepared by using the prepared total RNA to be tested, the above-mentioned primers and probe, and the commercially available real time detection PCR reagent kit (TaqMan EZ RT-PCR Core Reagent Kit (trade name), manufactured by PE Applied Biosystems), wherein the amounts shown in the table correspond to one reaction tube.

TABLE 1

| Component | Final Concentration |
|---|---|
| template RNA | |
| 5 × TaqMan EZ buffer A | 1× |
| 10 mM dATP | 300 μM |
| 10 mM dGTP | 300 μM |
| 10 mM dCTP | 300 μM |
| 20 mM dUTP | 600 μM |
| 10 μM UCP1 forward-side primer | 200 nM |
| 10 μM UCP1 reverse-side primer | 200 nM |
| 5 μM UCP1 probe | 100 nM |
| 10 μM G3PDH forward-side primer | 40 nM |
| 10 μM G3PDH reverse-side primer | 40 nM |
| 10 μM G3PDH probe | 100 nM |
| rTth DNA polymerase (2.5 U/μl) | 0.1 U/μl |
| AMP Erase UNG (1 U/μl) | 0.01 U/μl |
| 25 mM Mn(OAc)$_2$ | 3 mM |

Twenty-five micro liter of the above-prepared reaction solution was placed into a PCR Perkin Elmer Microamp Optical Tube (trade name, manufactured by PE Applied Biosystems), and the tube was closed with a cap. The tube was set on ABI PRISM 7700 Sequence Detection System (trade name, manufactured by PE Applied Biosystems), and subjected to reaction under the following conditions.

DNA contaminants were decomposed by UNG at 50° C. for 50 min, a reverse transcription process was carried out at 60° C. for 10 min, and the UNG was inactivated at 95° C. for 2 min. In the subsequent PCR reaction, a denaturation process was carried out at 95° C. for 15 sec, and an annealing process was carried out at 58° C. for 90 sec. (cycle number: 40 cycles). After the start of the reaction, fluorescence strength was automatically determined by a real-time process to measure the amount of UCP1 mRNA expression. The amount of the UCP1 mRNA expression was shown by a relative value calculated by setting the amount in the reference sample used as the blank control at 100, and the value was corrected by the amount of G3PDH mRNA expression.

The results are shown in FIG. 1. The amount of the UCP1 mRNA expression was increased to about 12 times that in the control by YM-16638 of a PPAR δ ligand (a compound having an effect to activate PPAR δ). This demonstrated that PPAR δ ligands strongly promotes such an expression. Since this experiment demonstrated that PPAR δ ligands upregulate specifically UCP1 genes, it became clear that the enhancing effect on the function of WAT by a PPAR δ ligand is attributable to a direct effect of the PPAR δ ligand to WAT. The fact that an extreme increase in UCP1 expression was observed in white adipocytes not only of rodents but also of humans showed that PPAR δ ligands are extremely effective for human diabetes and obesity.

(3) Measurement of the Amount of UCP2 mRNA Expression

By using the total RNA (about 0.1 μg) obtained in the above section (1) as a template, the amount of UCP2 mRNA expression was measured by real time polymerase chain reaction in the same manner as in the above section (2). As the PCR primers for human UCP2 gene, two kinds of oligonucleotides of 5'-CGCCAAATGAGCTTTGCCT-3' (the forward-side primer) and 5'-GCCCTTGGTGTAGAACTGTTTGA-3' (the reverse-side sense primer) were used. As the PCR probe, 5'-TGTCCGCATCGGCCTGTATGATTC-3' was used. The probe was labeled with FAM, a fluorescent dye.

Figure 2:
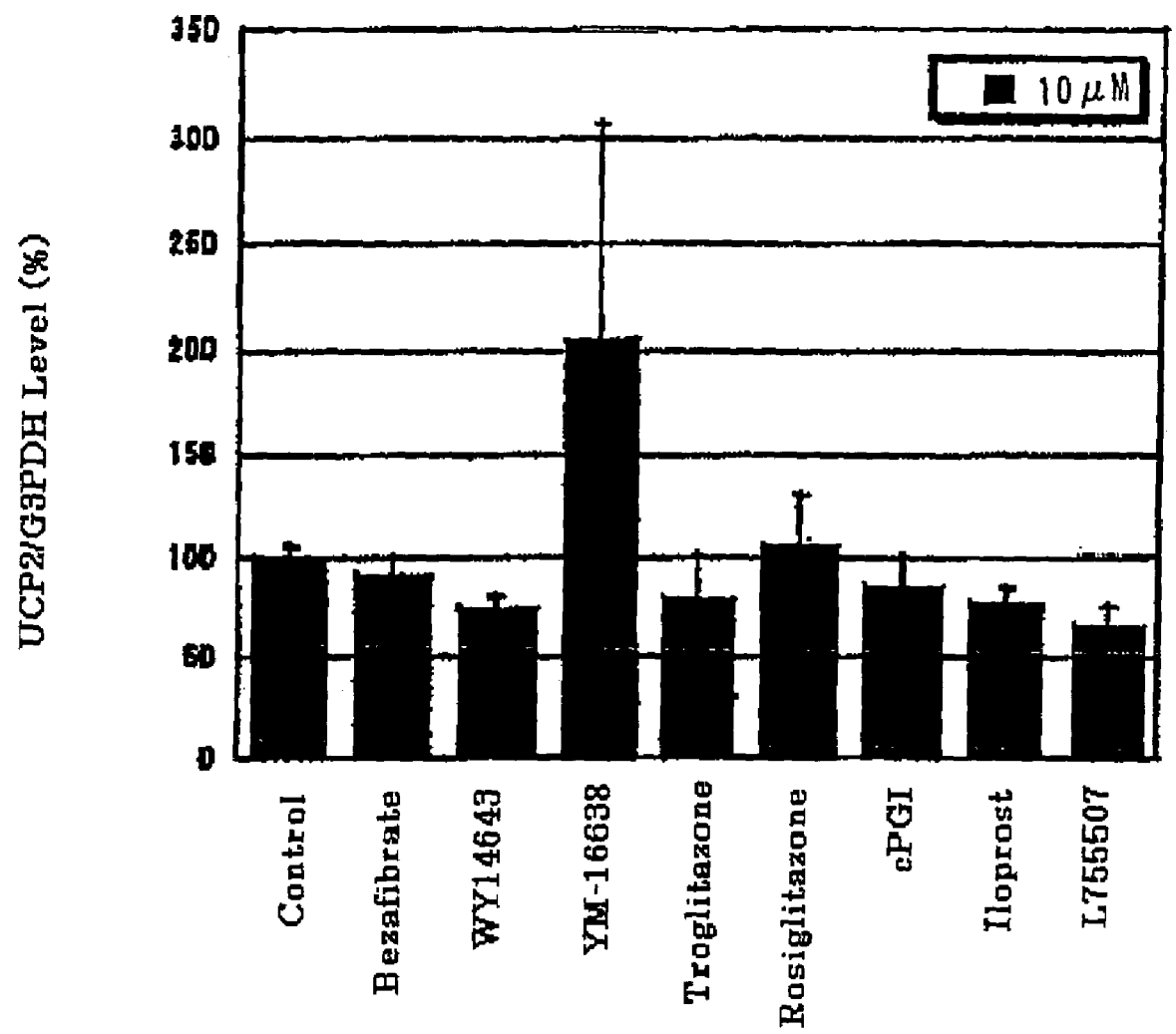
FIG. 2 shows the amount of expression of a UCP2 mRNA induced in human adipocytes by PPAR δ ligands or various kinds of test compounds.

The results are shown in FIG. 2. The amount of UCP2 mRNA expression was increased to about 2 times that in the control by YM-16638, a PPAR δ ligand (a compound having an effect to activate PPAR δ).

Example 2

Effect of Agents on Free Fatty Acid β-Oxidation in Human White Adipocytes

After human fully differentiated white adipocytes had been prepared in the same manner as in Example 1, the supernatant was removed, and 500 μl of a medium which had been prepared by adding adequate amounts of oleic acid and palmitic acid to an adipocyte medium so that their concentrations were 0.67 mM and 0.33 mM, respectively, was added. Various kinds of test compounds were added to the medium in such a manner that their final concentrations were 10 μM, and subsequently, [9,10(n)-$^3$H]palmitic acid (manufactured by Amersham Pharmacia, final concentration of 1 μCi/ml) was added to each well, and the cells were cultured at 37° C. for 48 hr. The test compounds were YM-16638 of a PPAR δ ligand, WY14643 of a PPAR α ligand, L755,507 of a β3 adrenergic receptor agonist and Rosiglitazone of a PPAR γ ligand. A control was prepared by adding DMSO, which was the solvent for the test compounds, in such a manner that the final concentration was 0.5%, and it was cultured in the same manner as the test compounds. In order to prevent the evaporation of $^3$H$_2$O produced by β-oxidation of the [9,10(n)-$^3$H] palmitic acid by the cells during culture, the culture plates were sealed with mini-culture filters (MS-30055) manufactured by Sumitomo Bakelite Co. Ltd.

After 48-hour culture, 200 μl of the supernatant of the medium was transferred to a 1.5-ml Eppendorf tube, 50 μl of 50% trichloroacetic acid was added, the tube was held on ice for 30 min to produce precipitates, and the mixture was centrifuged for 10 min at 15,000 rpm. Subsequently, in a 20-ml glass vial into which 500 μl of distilled water had been placed in advance, a cap-free 1.5-ml Eppendorf tube was placed, the total amount of the supernatant obtained above was placed into this Eppendorf tube, and the vial was tightly sealed with a polypropylene packing-attached lid. The vial was heated at 50° C. for 18 hr to saturate the inside of the vial with $^3$H$_2$O, the vial was centrifuged (1000 rpm, for 1 min) after cooling at 4° C. The culture supernatant remaining in the Eppendorf tube in the vial and the Eppendorf tube were discarded. Into the $^3$H$_2$O-containing distilled water remaining in the vial, 5 ml of a liquid scintillation cocktail (Ultima Gold, manufactured by Packard) was added, and radioactivity was measured after sufficient mixing.

Figure 3:
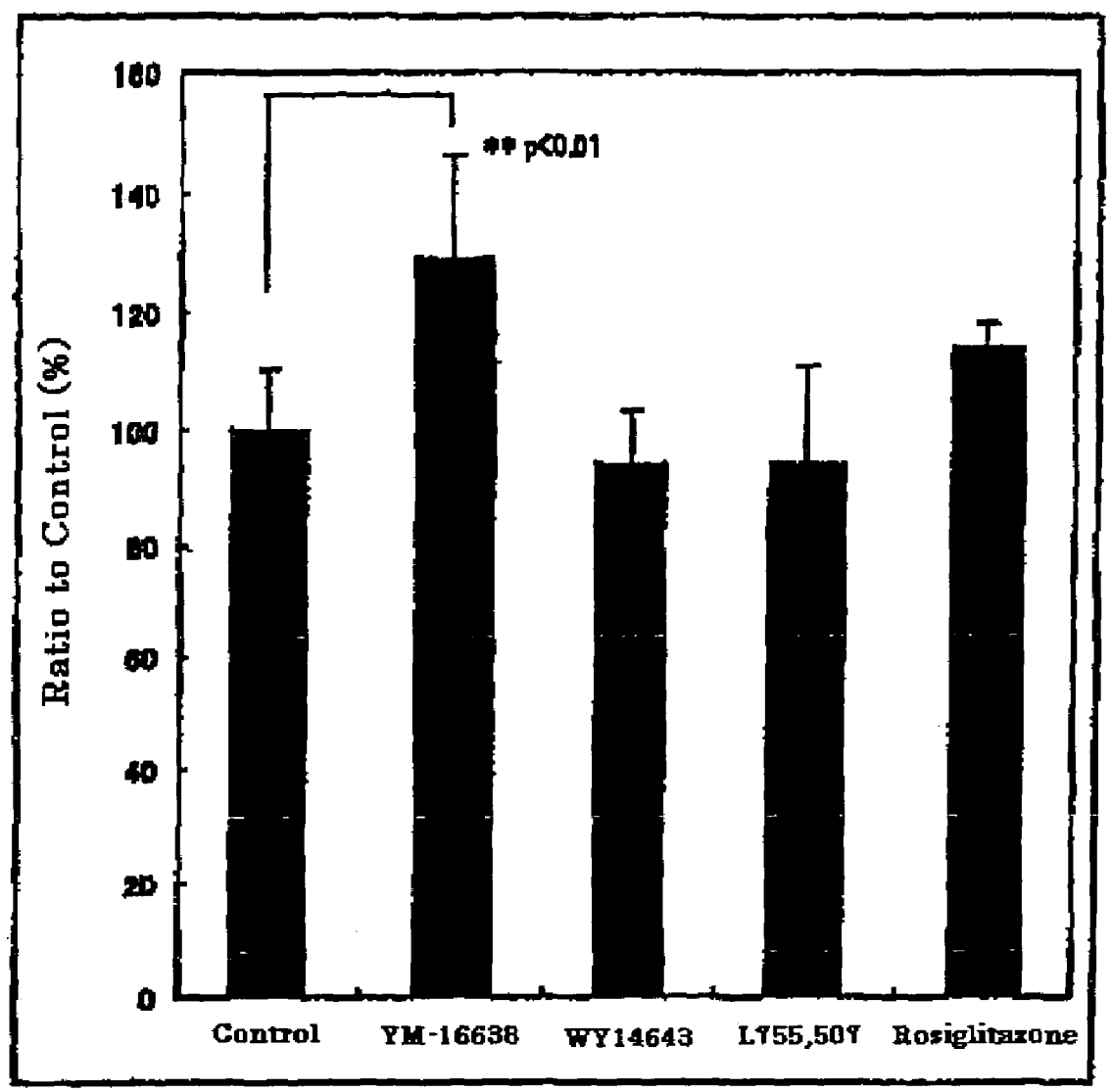
FIG. 3 shows the degree of enhancement of free fatty acid β-oxidation caused in human adipocytes by PPAR δ ligands or various kinds of test compounds.

The results are shown in FIG. 3. The β-oxidation in the cells was increased as much as 30% by 10 μM of YM16638 of a PPAR δ ligand. On the other hand, 10 μM of Rosiglitazone of a PPAR γ ligand had 15% enhancement, and 10 μM of WY14643 of a PPAR α ligand and 10 μM of L755,507 of a β3 adrenagic receptor agonist exhibited no enhancement of the β-oxidation. These results show excellent correlation with the upregulating effects of various kinds of PPAR ligands on the UCP1 mRNA expression observed in Example 1. That is, PPAR δ ligands increase the amount of UCP1 protein through the upregulation of the UCP1 gene expression, so that the β-oxidation that free fatty acids were utilized for substrates, the β-oxidation being one of the functions of UCP1, was enhanced. This demonstrates that PPAR δ ligands promote energy metabolism, and inhibit or reduce visceral fat accumulation. These results show that PPAR ligands are effective against human diabetes and obesity.

INDUSTRIAL FIELD OF APPLICATION

The present invention provides a substance having a thermogenesis enhancing effect and the like, and provides an agent such as an antidiabetic agent, an antiobestic gent, or a visceral accumulated fat-lowering agent or visceral fat accumulation-inhibiting agent containing the substance.

The invention claimed is:

1. A method for screening for a compound that enhances thermogenesis by determining whether the compound activates PPAR δ, said method comprising:
   contacting said compound with PPAR δ,
   detecting whether PPAR δ is activated by said compound,
   wherein said compound enhances thermogenesis if said PPAR δ is activated by said compound.

2. A method for screening for a compound that enhances uncoupling respiration in mitochondria in mitochondria-containing cells, said method comprising:
   contacting said compound with PPAR δ,
   detecting whether PPAR δ is activated by said compound,
   wherein said compound enhances uncoupling respiration in mitochondria if said PPAR δ is activated by said compound.

3. A method for screening for a compound that enhances proton leak in inner membranes of mitochondria in mitochondria-containing cells, said method comprising:
   contacting said compound with PPAR δ,
   detecting whether PPAR δ is activated by said compound,
   wherein said compounds enhances proton leak in inner membranes of mitochondria if said PPAR δ is activated by said compound.

4. A method for screening for a compound that increases the expression of UCP1 in mitochondria-containing cells, said method comprising:
   contacting said compound with PPAR δ,
   detecting whether PPAR δ is activated by said compound, wherein said compound increases the expression of UCP1 if said PPAR δ is activated by said compound.

5. A method for screening for a compound that enhances fatty acid β-oxidation in mitochondria-containing cells, said method comprising:
   contacting said compound with PPAR δ,
   detecting whether PPAR δ is activated by said compound,
   wherein said compound enhances fatty acid β-oxidation if said PPAR δ is activated by said compound.

6. The method for screening for a compound according to Claim 1, wherein activation of said PPAR δ is detected with a reporter gene.

7. The method for screening for a compound according to any one of claims 2 to 5, wherein activation of said PPAR δ is detected with a reporter gene.

8. The method according to Claim 7, wherein the mitochondria-containing cell is an adipocyte or a skeletal muscle cell.

9. The method according to Claim 7, wherein the mitochondria-containing cell is an adipocyte.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Forward-side Primer of PCR for Human UCP1 Gene

<400> SEQUENCE: 1
aacccacaga ggtcgtgaaa g                                             21

<210> SEQ ID NO 2
<211> LENGTH: 21
<212> TYPE: DNA
<213> ORGANISM: Artificial Sequence
<220> FEATURE:
<223> OTHER INFORMATION: Reverse-side Primer of PCR for Human UCP1 Gene

<400> SEQUENCE: 2
cgtgtagcga ggtttgattc c                                             21

<210> SEQ ID NO 3
<211> LENGTH: 27
<212> TYPE: DNA
<213> ORGANISM: Artificial Sequence
<220> FEATURE:
<223> OTHER INFORMATION: Probe of PCR for Human UCP1 Gene

<400> SEQUENCE: 3
cagacttcaa gcatagagcc atctcca                                       27

<210> SEQ ID NO 4
<211> LENGTH: 19
<212> TYPE: DNA
<213> ORGANISM: Artificial Sequence
<220> FEATURE:
<223> OTHER INFORMATION: Forward-side Primer of PCR for Human UCP2 Gene

<400> SEQUENCE: 4
cgccaaatga gctttgcct                                                19

<210> SEQ ID NO 5
<211> LENGTH: 23
<212> TYPE: DNA
<213> ORGANISM: Artificial Sequence
<220> FEATURE:
<223> OTHER INFORMATION: Reverse-side Primer of PCR for Human UCP2 Gene

<400> SEQUENCE: 5
```

```
gcccttggtg tagaactgtt tga                                          23

<210> SEQ ID NO 6
<211> LENGTH: 24
<212> TYPE: DNA
<213> ORGANISM: Artificial Sequence
<220> FEATURE:
<223> OTHER INFORMATION: Probe of PCR for Human UCP2 Gene

<400> SEQUENCE: 6
tgtccgcatc ggcctgtatg attc                                         24
```